(12) United States Patent
Luinstra et al.

(10) Patent No.: US 7,145,022 B2
(45) Date of Patent: Dec. 5, 2006

(54) CATALYST FOR THE CARBONYLATION OF OXIRANES

(75) Inventors: Gerrit Luinstra, Mannheim (DE); Bernhard Rieger, Oberelchingen (DE); Markus Allmendinger, Deggingen (DE)

(73) Assignee: BASF Aktiengesellschaft (DE)

( * ) Notice: Subject to any disclaimer, the term of this patent is extended or adjusted under 35 U.S.C. 154(b) by 131 days.

(21) Appl. No.: 10/523,264

(22) PCT Filed: Jul. 31, 2003

(86) PCT No.: PCT/EP03/08478

§ 371 (c)(1),
(2), (4) Date: Mar. 7, 2005

(87) PCT Pub. No.: WO2004/012861

PCT Pub. Date: Feb. 12, 2004

(65) Prior Publication Data

US 2005/0240032 A1 Oct. 27, 2005

(30) Foreign Application Priority Data

Aug. 1, 2002 (DE) .................. 102 35 316

(51) Int. Cl.
C07D 305/12 (2006.01)
(52) U.S. Cl. .................................. 549/328
(58) Field of Classification Search ................ 549/328
See application file for complete search history.

(56) References Cited

U.S. PATENT DOCUMENTS

| 3,260,738 A | 7/1966 | McClure et al. |
| 4,620,033 A | 10/1986 | Isshiki et al. |
| 6,084,124 A | 7/2000 | Slaugh et al. |
| 6,262,278 B1 | 7/2001 | Jacobsen et al. |
| 2003/0162961 A1 | 8/2003 | Coates et al. |

FOREIGN PATENT DOCUMENTS

| EP | 0 577 206 | 1/1994 |
| EP | 0 688 806 | 12/1995 |
| GB | 1020575 | 2/1966 |
| JP | 9-169753 | 6/1997 |
| WO | WO-00/09463 | 2/2000 |
| WO | WO-03/050154 | 6/2003 |
| WO | WO-2004/012860 | 2/2004 |

OTHER PUBLICATIONS

Kamiya et al., "The Reaction Of Small Ring Compound With Carbon Monoxide The Carbonylation Of Oxirane", *Chemistry Letters*, pp. 1549-1552 (1980).
Chem. Abstracts, 117, No. 26, Abstract No. 263541 (1992).
Ohba et al., "Oxalate-Bridged Dinuclear Cr(III)-M(II) (M = Cu, Ni, Co, Fe, Mn) Complexes: Synthesis, Structure, and Magnetism", *Inorg. Chem.*, vol. 32, pp. 5385-5390 (1993).
Atwood et al., "A New Class of Aluminum Cations upon Tetradentate ($N_2O_2$) Chelating Ligands", *Inorg. Chem.*, vol. 35, pp. 63-70 (1996).
Hinterding et al., "Regioselective Carbomethoxylation of Chiral Epoxides: A New Route to Enantiomerically Pure β-Hydroxy Esters", *J. Org. Chem.*, vol. 64, pp. 2164-2165 (1999).
Jacobsen, "Asymmetric Catalysis of Epoxide Ring-Opening Reactons", *Acc. Chem. Res.*, vol. 33, pp. 421-431 (2000).
Lee et al., "Synthesis of β-Lactones by the Regioselective, Cobalt and Lewis Acid Catalyzed Carbonylation of Simple and Functionalized Epoxides", *J. Org. Chem.*, vol. 66, pp. 5424-5426 (2001).
Paddock et al., "Chemical $CO_2$ Fixation: Cr(III) Salen Complexes as Highly Efficient Catalysts for the Coupling of $CO_2$ and Epoxides", *J. Am. Chem. Soc.*, vol. 123, pp. 11498-11499 (2001).
Getzler et al., "Synthesis of β-Lactones: A Highly Active and Selective Catalyst for Epoxide Carbonylation", *J. Am. Chem. Soc.*, vol. 24, pp. 1174-1175, (2002).

*Primary Examiner*—Taofiq Solola
(74) *Attorney, Agent, or Firm*—Connolly Bove Lodge & Hutz

(57) ABSTRACT

Lactones are prepared by catalytic carbonylation of oxiranes using a catalyst system comprising
a) at least one carbonylation catalyst A comprising uncharged or anionic transition metal complexes of metals of groups 5 to 11 of the Periodic Table of the Elements and
b) at least one chiral Lewis acid B,
with the exception of [(salph)Al(THF)$_2$][Co(CO)$_4$], as catalyst.

6 Claims, No Drawings

US 7,145,022 B2

CATALYST FOR THE CARBONYLATION OF OXIRANES

RELATED APPLICATIONS

This application is a national stage application (under 35 U.S.C. 371) of PCT/EP2003/008478 filed Jul. 31, 2003 which claims benefit to German application Serial No. DE 102 35 316.6 filed Aug. 1, 2002.

The present invention relates to the preparation of lactones by catalytic carbonylation of oxiranes in the presence of a catalyst system, to a corresponding catalyst system and to its use.

In particular, the invention relates to the preparation of enantiomerically enriched four-membered ring lactone mixtures from racemic epoxides by catalytic carbonylation. The catalysis is achieved by means of a catalyst system comprising two components. The optically enriched mixture of R- and S-lactones can be converted into a biodegradable polyester.

Lactones are valuable compounds for preparing biodegradable polyesters, as described, for example, in EP-A 0 688 806. These polyesters are widely used, for example as polyol in polyurethane production or as material of construction.

The properties of such β-alkylhydroxyalkanoate polyesters depend greatly on the stereoregularity. Thus, for example, atactic polyhydroxybutyrate (PHB) is a viscous oil, while isotactic PHB is a solid which can be used as a material of construction. Isotactic PHB can be obtained from enantiomerically pure butyrolactone. Enantiomerically pure butyrolactone can be prepared either by means of a complicated organic synthesis using protective groups or by a biochemical route. However, the synthetic route to these compounds is, particularly for large-scale industrial applications, very complex and costly. In addition, the purification is also complicated.

Furthermore, the processing of pure isotactic PHB by means of injection molding is problematical, since the decomposition temperature is very close to the melting point. In addition, pure isotactic PHB is brittle. A more readily processable and tougher PHB is not purely isotactic, but instead contains proportions of atactic structural elements. Such a PHB can be obtained from mixtures of R- and S-butyrolactones by polymerization. It is therefore desirable to prepare lactone mixtures in which one enantiomer is present in an excess over the other enantiomer. The preparation of lactones by catalytic carbonylation of simple and substituted oxiranes is known per se. The products are often not the desired lactones, or the reaction conditions or the starting materials do not permit efficient preparation or isolation of lactones. The compounds can frequently be obtained only by means of complicated and costly syntheses.

JP-A-09 169 753 describes the carbonylation of epoxides to lactones over $CO_2(CO)_8$ as catalyst in a flow-through reactor. The conversions are only 30%. This means that a separation and recirculation facility is required to achieve high yields and purity of the lactone.

GB-A-1,020,575 relates to a process for preparing polymers of β-lactones. Carbon monoxide and a 1,2-epoxide are reacted to form a β-lactone as intermediate. Octacarbonyldicobalt is used as catalyst in this reaction. In addition, a promoter selected from among metal halides such as potassium iodide and quaternary ammonium halides such as tetraethylammonium bromide can be added. However, the yields of lactone are less than 10%, and the main fractions of the products are polyhydroxypropionic esters. In addition, the reaction is carried out in a complicated manner with a plurality of pressure stages.

EP-B-0 577 206 relates to the carbonylation of epoxides over a catalyst system comprising a cobalt source and a hydroxy-substituted pyridine compound, in particular 3-hydroxypyridine or 4-hydroxypyridine. The carbonylation is preferably carried out in the presence of a hydroxy compound such as water or alcohols. The activities of the catalysts used are relatively low, and isolation of the lactones is not described. It was also observed that a change in the reaction mixture occurred after the carbonylation had ended. Polymerization of the lactone takes place within 24 hours. This indicates that the lactone is not unreactive in the reaction mixture. It is also known that lactones can be polymerized in the presence of pyridines.

Chemistry Letters 1980, pages 1549 to 1552, relates to the reaction of epoxides with carbon monoxide over a rhodium complex as catalyst. The yields are not more than 70%. J. Org. Chem. 2001, 66, pages 5424 to 5426, describes the synthesis of β-lactones by carbonylation of epoxides over cobalt and Lewis acid catalysts. As catalyst, use is made of a system comprising $PPNCo(CO)_4$ and $BF_3.Et_2O$. The yields range from 7 to 86%. However, the reaction time is from 7 to 24 hours and the use of large amounts of catalyst is necessary.

J. Am. Chem. Soc. 124, No. 7, 2002, pages 1174 to 1175, describes the preparation of β-lactones by carbonylation of epoxides. The catalyst used is a mixture of aluminum salts and a tetracarbonylcobaltate. A mixture of lactones having an excess of one enantiomer is not obtained.

J. Org. Chem. 1999, 64, pages 2164 to 2165, describes the preparation of chiral epoxides and hydroxy alcohols from racemic epoxides using a chiral Co(salen)(N,N-bis-[3,5-di-t-butylsalicylidene]-1,2-diaminocyclohexane). In a subsequent step, the epoxides are reacted with a mixture of $Co/H_2$ and propanols in the presence of octacarbonyldicobalt to give chiral acetals. Two steps are thus necessary for the preparation of carbonylated compounds based on epoxides. This is complicated, does not give a lactone and, in addition, half of the racemic oxirane is lost.

It is an object of the present invention to provide an uncomplicated and efficient process for the preparation and isolation of optically enriched β-lactones.

We have found that this object is achieved by a process for preparing lactones by catalytic carbonylation of oxiranes using a catalyst system comprising
  a) at least one carbonylation catalyst A comprising uncharged or anionic transition metal complexes of metals of groups 5 to 11 of the Periodic Table of the Elements and
  b) at least one chiral Lewis acid B, with the exception of $[(salph)Al(THF)_2][Co(CO)_4]$, as catalyst.

According to the present invention, it has been found that a catalyst system comprising two components, viz. a carbonylation catalyst A and a chiral Lewis acid B, leads to optical enrichment in the carbonylation of oxiranes to lactones.

In addition, it has been found that the combination of the carbonylation catalyst A with the chiral Lewis acid B allows efficient catalysis of the carbonylation of oxiranes to lactones under mild conditions.

The lactones obtained can advantageously be used for the preparation of biodegradable polyesters which can be used as polyol in polyurethane production or as materials of construction.

In the catalyst system used according to the present invention, preference is given to from 0.1 to 1000 mol, particularly preferably from 1 to 10 mol, of the component B being present per mole of component A.

Transition metal complexes A used as carbonylation catalyst can in principle be any uncharged complexes based on metals of groups 5 to 11 of the Periodic Table of the Elements in which the central metal bears a formal charge of 0. Examples of suitable metals are vanadium, ruthenium, chromium, molybdenum, tungsten, manganese, rhenium, iron, osmium, cobalt, iridium, rhodium and nickel. Such complexes can also be generated in situ, cf. EP-A 0 577 206. Particular preference is given to Re, Co, Ru, Rh, Fe, Ni, Mn, Mo, W or mixtures thereof, in particular Co.

In the uncharged transition metal complex (A), the ligands are generally present as uncharged ligands. The number of ligands depends on the respective metal and is determined by the coordinative saturation of the transition metal in the ground state. Suitable uncharged ligands are, for example, carbon monoxide, nitro, nitroso, carbonate, ether, sulfoxide, amide, nitrile or phosphine ligands. These ligands are generally coordinated to the transition metal via a free electron pair. Preference is given to using carbon monoxide as ligand. It is also possible for different ligands to be present together in a transition metal compound (A), as in $Co_2(CO)_6(PMe_2Ph)_2$. Preferred transition metal complexes (A) are $Co_2(CO)_8$, $Ru_3(CO)_{12}$, $Rh_4(CO)_{12}$, $Rh_6(CO)_{16}$, $Co_4(CO)_{12}$, $Fe_2(CO)_{10}$, $Fe_2(CO)_9$, $Ni(CO)_4$, $Mn_2(CO)_{10}$, $Mo(CO)_6$ and $W(CO)_6$ or mixtures thereof. Particular preference is given to $Ru_3(CO)_{12}$, $Co_4(CO)_{12}$, $Co(CO)_3(NO)$, $Ni(CO)_4$ and $Mn_2(CO)_{10}$, in particular $Co_2(CO)_8$.

It is also possible to use mixtures of various uncharged complexes.

The preparation of the uncharged transition metal complexes A is generally known to those skilled in the art and is described, for example, in F. G. Stone, E. W. Abel and G. Wilkinson, "Comprehensive Organometallic Chemistry—The Synthesis, Reactions and Structures of Organometallic Compounds", Pergamon Press, Oxford, 1982, for example in Vol. 5. Furthermore, such complexes are also commercially available.

For the purposes of the present invention, transition metal complexes (A) include compounds in which at least one central metal or a ligand unit bears a formal negative charge. Suitable anionic transition metal compounds (A) have a central metal from groups 5 to 11, preferably from groups 8 to 10, of the Periodic Table of the Elements. Possible metals are, for example, cobalt, iron, rhodium and ruthenium. Particular preference is given to using transition metal complexes (A) based on the metals cobalt, ruthenium and rhodium. It is possible to use mononuclear or multinuclear complexes A.

In the anionic transition metal complex A, the ligands are usually also present as uncharged ligands. The number of ligands depends on the respective metal and is determined by the coordinative saturation of the transition metal in the ground state. Examples of suitable uncharged ligands are carbon monoxide, nitro, nitroso, carbonate, ether, sulfoxide, amide, nitrile or phosphine ligands. These ligands are generally coordinated to the transition metal via a free electron pair. Preference is given to using carbon monoxide as ligand. It is also possible for different ligands to be present together in an anionic transition metal compound A, for example as in $[P(Ph)_3]Co(-1)(CO)_3$, $[P(Me_2Ph)]Co(-1)(CO)_3$, $Co(-1)(CO)_3(CNPh)$. These compounds, too, can be generated in situ.

Suitable anionic transition metal complexes A have, for example, the formula (I):

$$(M_\alpha^{(n+)})_m[M_\beta(L)_4]_l \qquad (I),$$

where the variables and indices have the following meanings:

$M_\beta$ is a transition metal of groups 8 to 10 of the Periodic Table of the Elements, in particular cobalt or rhodium, bearing the formal charge $-1$, L is $PR_3$, $P(OR)_3$ $NR_3$, $SR_2$, $OR_2$, CO, R—CN, R—$NO_2$, (RO)(R'O)C=O, (R)(R')C=O, (R)C=O(OR'), in particular CO, $M_\alpha$ is a metal of group 1 or 2 of the Periodic Table of the Elements, Zn or Hg, in particular Na, K, Cs, Mg, Ca, Zn and Hg, bis(triarylphosphine)iminium, trityl or $T(R)_4$ where T is N, P or As, in particular N, R, R' are each, independently of one another, H, alkyl, aryl, alkaryl or aralkyl, n, m are each 1 or 2 and l is n×m.

Possible radicals R, R' are, for example, hydrogen, straight-chain or branched $C_1$–$C_{10}$-alkyl such as methyl, ethyl, n- or i-propyl, n-, i- or t-butyl or n- or i-pentyl, $C_6$–$C_{14}$-aryl such as phenyl or naphthyl or alkylaryl having from 1 to 10 carbon atoms in the alkyl part and from 6 to 14 carbon atoms in the aryl part, e.g. benzyl. Suitable aromatic radicals also include heterocycles and may be, for example 5- or 6-membered monocycles such as pyridyl and phenyl, and also fused systems such as anthracene.

Among the nonmetallic cations M, preference is given to tetraphenyl-, tetramethyl-, tetraethyl- and tetra-n-butyl-ammonium, -phosphonium and -arsenium and also bis(triarylphosphine)iminium. Particularly useful aryl radicals in the bis(triarylphosphine)iminium cation are phenyl and naphthyl, with bis(triphenylphosphine)iminium being preferred.

Possible metallic cations $M_\alpha$ include alkali metal and alkaline earth metal cations. Preference is given to using lithium, sodium, potassium and cesium.

Use is advantageously made of anionic transition metal complexes A selected from the group consisting of $Li[Co(CO)_4]$, $Na[Co(CO)_4]$, $K[Co(CO)_4]$, $Cs[Co(CO)_4]$, $(R_4N)[Co(CO)_4]$, $(R_4P)[Co(CO)_4]$, $(R_4As)[Co(CO)_4]$, $(PPN)[Co(CO)_4]$, $Li[Rh(CO)_4]$, $Na[Rh(CO)_4]$, $K[Rh(CO)_4]$, $Cs[Rh(CO)_4]$, $(R_4N)[Rh(CO)_4]$, $(R_4P)[Rh(CO)_4]$, $(R_4As)[Rh(CO)_4]$, $(PPN)[Rh(CO)_4]$, $Li[Ir(CO)_4]$, $Na[Ir(CO)_4]$, $K[Ir(CO)_4]$, $Cs[Ir(CO)_4]$, $(R_4N)[Ir(CO)_4]$, $(R_rP)[Ir(CO)_4]$, $(R_4As)[Ir(CO)_4]$, $(PPN)[Ir(CO)_4]$, $Li_2[Fe(CO)_4]$, $Na_2[Fe(CO)_4]$, $K_2[Fe(CO)_4]$, $Cs_2[Fe(CO)_4]$, $(R_4N)_2[Fe(CO)_4]$, $(R_4P)_2[Fe(CO)_4]$, $(R_4As)_2[Fe(CO)_4]$, $(PPN)_2[Fe(CO)_4]$, $(PPN)[HFe(CO)_4]$ and $(PPN)_2[Fe_2(CO)_8]$, where R is methyl, ethyl, n- or i-propyl, n-, i- or t-butyl, phenyl or benzyl.

Among anionic complexes A containing cobalt in the oxidation state $-1$, particular preference is given to tetraphenylphosphonium tetracarbonylcobaltate, tetraphenylarsenium tetracarbonylcobaltate, tetraphenylammonium tetracarbonylcobaltate, tetraethylphosphonium tetracarbonylcobaltate, tetraethylarsenium tetracarbonylcobaltate and tetraethylammonium tetracarbonylcobaltate and also sodium tetracarbonylcobaltate.

It is of course also possible to use mixtures of anionic and/or uncharged transition metal complexes A.

The preparation of anionic transition metal complexes is generally known to those skilled in the art. Suitable preparative methods may be found, for example, in F. G. Stone, E. W. Abel and G. Wilkinson, "Comprehensive Organometallic Chemistry—The Synthesis, Reactions and Structures of Organometallic Compounds", Pergamon, Oxford, 1982 and F. G. Stone, E. W. Abel and G. Wilkinson, "Comprehensive Organometallic Chemistry II—A Review of the Literature 1982–1994", Pergamon Press, Oxford for example in Vol. 8. Furthermore, such complexes are also commercially available.

The molar ratio of anionic complex or uncharged complex (A) in the reaction mixture is usually in the range from 0.01 to 100 mol %, preferably from 0.1 to 50 mol %, particularly preferably from 0.2 to 10 mol %, based on the amount of oxirane used.

As chiral Lewis acids B, use is generally made of one or more compounds of elements of groups 2 to 13. These compounds are coordinatively unsaturated or allow a ligand to be split off (reversibly) under the reaction conditions of the carbonylation so that unsaturation can occur. Lewis acids B preferably bind ligands which do not participate in the reaction but exercise a controlling action on the carbonylation. The ligand-metal units are chiral and are preferably not present as a racemic mixture but in enantiomerically pure form and with an enantiomeric excess in the reaction mixture.

Compounds B are, for example, compounds $L_nMX_m$, where

M=Mg, Ca, Sc, Y, rare earth element, Ti, V, Cr, Mn, Fe, Co, Ni, Cu, Zn, Al, Ga, Zr, Nb, Mo, Ru, Rh, Pd, Ag, Cd, In, Hf, Ta, W, Re, Os, Ir, Pt, Au, Hg, Tl, Pb. Preferred metals M are Ti, Zr, Hf, Cr, Mo, W, Co, Rh, Ir, Ni, Pd, Cu, Cd, Al, Mg, Zn, Fe. Particularly preferred metals M are Cr, Co, Ti, Fe, Ni, Pd;

X=an anion, for example halide, sulfate, sulfite, nitrate, nitrite, carboxylate, sulfide, phosphate, sulfonate, borate, preferably Ci, sulfonate or carboxylate;

L(n)=phosphine, cyclopentadienyl or ansa-ligands, salen, imines, oxazoline, alkoxide, phenoxide, carboxylate, where various L can also be joined to to one another and L is chiral. Preferred ligands are salen (1,2-cyclohexanediamino-N,N-bis-3,5-di-t-butylsalicylidene), diphosphines (for example (2S,4S)-(–)-(diphenylphosphino)-2-(diphenylphosphinomethyl)pyrrolidine, (R)-(+)-2,2'-bis(diphenylphosphino)-1,1'-binaphthyl (binap), R-(+)-1,2-bis(diphenylphosphino)propane, (4R,5R)-(–)-o-isopropylidene-2,3-dihydroxy-1,4-bis(diphenylphosphino)butane (diop), (1S,2S)-(+)-1,2-bis(diphenylphosphinomethyl)cyclohexane, (–)-(R)-N,N-dimethyl-1-[(S)-1',2-bis(diphenylphosphino)ferrocenyl]ethylamine, (2R,3R)-(+)-bis(diphenylphosphino)butane, (+)-1,2-bis[(2S,5S)-2,5-dimethylphospholano]benzene, (S)-1((R)-1',2-bis(diphenylphosphino)ferrocenyl)ethanol, (R)-(–)-1-[(S)-2-(diphenylphosphino)ferrocenyl]ethyl-dicyclohexylphosphine, (1S,2S)-(+)-1,2-bis[(n-diphenylphosphino)amino]cyclohexane), oxazolines (for example 1,2-bis(2,4-dimethyl-2-oxazolin-2-yl)ethane, (S,S)-2,2'-bis(4-benzyl-2-oxazoline), (S,S)-2,2'-(2,6-pyridinediyl)bis(4-isopropyl-2-oxazoline), (S,S)-(–)-2,2'-(dimethylmethylene)bis(4-tert-butyl-2-oxazoline), (4R,5S,4'R,5'S)-2,2'-methylene-bis(4,5-diphenyl-2-oxazoline), ethylenebis(4,5,6,7-tetrahydro-1-indenyl), binaphthol, amino acids. Possible further ligands are known to those skilled in the art from asymmetric catalysis using homogenous organometallic compounds.

A preferred compound B is Cr(1,2-cyclohexanediamino-N,N-bis-3,5-di-t-butylsalicylidene) chloride or acetate.

Suitable oxirane compounds are ethylene oxide and substituted epoxides. These are usually compounds having the formula (II):

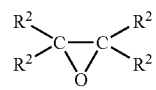

(II)

In this formula, the radicals $R^2$ are each, independently of one another, hydrogen, halogen, a nitro group —$NO_2$, a cyano group —CN, an ester group —$COOR^3$ or a hydrocarbon group having from 1 to 32 carbon atoms which may be substituted. The radicals $R^2$ in a compound (II) can all be the same, some of them can be the same or they can be four different radicals. $R^3$ can be $C_{1-12}$-alkyl, aryl.

Preference is given to using geminally substituted epoxides, particularly preferably epoxides which are substituted only in the 1 position.

Suitable hydrocarbon groups are, for example, $C_{1-32}$-alkyl such as methyl, ethyl, i- or n-propyl, i-, n- or t-butyl, n-pentyl or n-hexyl, $C_{2-20}$-alkenyl such as propenyl or butenyl, $C_{3-20}$-cycloalkyl such as cyclopropyl, cyclobutyl, cyclopentyl or cyclohexyl, $C_{6-18}$-aryl such as phenyl or naphthyl, and $C_{7-20}$-arylalkyl, e.g. benzyl. It is also possible for two radicals $R^2$ located on different carbon atoms of the epoxy group to be joined to one another and thus form a $C_{3-20}$-cycloalkylene group.

Possible substituents by which the $C_{1-32}$-hydrocarbon group and also R above can be substituted are, in particular, the following groups: halogen, cyano, nitro, thioalkyl, tert-amino, alkoxy, aryloxy, arylalkyloxy, carbonyldioxyalkyl, carbonyldioxyaryl, carbonyldioxyarylalkyl, alkoxycarbonyl, aryloxycarbonyl, arylalkyloxycarbonyl, alkylcarbonyl, arylcarbonyl, arylalkylcarbonyl, alkylsulfinyl, arylsulfinyl, arylalkylsulfinyl, alkylsulfonyl, arylsulfonyl and arylalkylsulfonyl.

As oxirane compound, preference is given to using ethylene oxide, propylene oxide, butylene oxide (1-butene oxide, BuO), cyclopentene oxide, cyclohexene oxide (CHO), cycloheptene oxide, 2,3-epoxypropyl phenyl ether, epichlorohydrin, epibromohydrin, i-butene oxide (IBO), styrene oxide or acrylic oxides. Particular preference is given to using ethylene oxide (EO), propylene oxide (PO), butylene oxide or i-butene oxide, very particularly preferably ethylene oxide or propylene oxide or a mixture thereof.

In general, a solvent is also present, usually in small amounts, and has the main purpose of introducing the catalyst compound into the polymerization vessel or keeping the oxirane or the lactone in solution.

The reaction can also be carried out in the absence of solvent as a gas-phase polymerization when the catalyst components (A) and (B) are applied to a particulate support material, for example silica or aluminum oxide.

Suitable solvents include, in particular, polar solvents such as ether compounds, for example tetrahydrofuran, diethyl ether, dioxane, 2,5,8-trioxanone, anisole, dimethoxyethane (DME) and diethylene glycol dimethyl ether (diglyme), tetraglyme and also dimethylformamide or dimethyl sulfoxide.

The carbonylation is usually carried out under superatmospheric carbon monoxide pressure. The carbon monoxide pressure is generally in a range from 2 to 250 bar, in particular from 10 to 80 bar.

Suitable reaction temperatures range from room temperature, i.e. about 25° C., to 150° C. and are preferably in the range from 35 to 90° C.

The polymerization according to the process of the present invention can be carried out either batchwise or continuously.

In general, the transition metal complexes (A) and the Lewis acid (B) are firstly introduced into the reaction vessel either individually, simultaneously or in premixed form, if appropriate with cooling. It is also possible, if desired, for the oxirane compound to be mixed into the solution/suspension of the catalyst components before the latter is transferred to the reaction vessel. Furthermore, the oxirane compound can also be introduced directly into the reaction vessel. The order of addition is generally not critical to the process. The carbonylation is preferably carried out under inert conditions, i.e. in the absence of moisture and air.

Termination of the carbonylation and separation and purification of the lactones can be carried out by generally known methods. For example, the lactone can be isolated in a simple fashion by distillation or crystallization.

The process of the present invention enables 3-hydroxypropiolactones to be obtained from the corresponding oxirane compounds. Depending on the Lewis acid, the products are lactones whose degree of optical purity corresponds directly to the effectiveness of the Lewis acid and the percentage conversion of the oxirane. Use of the lactones prepared in this way make it possible to control the thermoplastic property profile of the biodegradable polymers whose properties can be set very simply and specifically for desired applications.

The lactones are preferably mixtures of S- and R-lactones containing an excess of one enantiomer. Preference is given to an enantiomeric excess, in particular of the R-enantiomer such as R-butyrolactone, of from 8 to 98%, particularly preferably from 15 to 80%.

The invention also provides a process for preparing the catalyst used according to the present invention by mixing the components A und B. Furthermore, the invention relates to the use of the catalyst in carbonylation reactions.

The invention makes it possible to prepare biodegradable materials in the form of polyhydroxyalkanoates via lactones as intermediates from chemicals which are available on a large industrial scale. Such polymers have the character of a material of construction when they have reliable stereoregularity. This can be achieved by means of the catalyst system via the optical purity of the enantiomers (enattiomer mixtures). These are, for example, present in biologically produced material.

The invention is illustrated by the following examples.

EXAMPLES

Reagents

The reagents used come from Fluka, Aldrich or Merck and were used without further purification. The solvents were obtained in dried form and were in each case degassed and saturated with $N_2$ before use. Cr-salen complex (1): (1R,2R)-(−)-[1,2-cyclohexanediamino-N,N'-bis(3,5-di-t-butylsalicylidene)]chromium(III) chloride was obtained from Strem Chemicals. Racemic propylene oxide (PO) and octacarbonyldicobalt are commercial products from Fluka which were used in the carbonylation without further purification. The $Co(CO)_4$ salts used were prepared from octacarbonyldicobalt in a "single-vessel synthesis".

Cr-salen complex (2): 1,2-benzenediamino-N,N'-bis(3,5-di-t-butylsalicylidene)]-chromium(II) chloride was synthesized as described in the literature [Paddock, R. L.; Nguyen, S. T. *J. Am. Chem. Soc.* 2001, 123, 11498–11499].

The carbonylation reactions were carried out in a 100 ml Parr steel autoclave or in a 250 ml Büchi autoclave equipped with a ReactIR™ SiComp™ dipper system from Mettler Toledo. This makes on-line analysis of the reaction mixture possible.

Analysis

NMR spectra were recorded using a Bruker instrument (AMX 400). NMR shift reagent (2): (S)-(+)-2,2,2-trifluoro-1-(9-anthryl)ethanol.

Carbonylation 1

The Cr-salen complex 1 (242 mg, 0.39 mmol) was added to $Na[Co(CO)_4]$ (0.39 mmol) in rac-propylene oxide (8 ml, 320 eq.) while cooling in ice and under an argon atmosphere. To charge the steel autoclave (100 ml), it was firstly evacuated and the starting materials were introduced under a countercurrent of argon. After the solution had been introduced, a carbon monoxide pressure of 60–65 bar was set, and the carbonylation was carried out at 25° C. over a period of ½ hour (the reaction mixture initially heated up significantly). The reaction was stopped by cooling in ice and reducing the pressure to ambient pressure, and the resulting reaction solution was analyzed. An NMR spectrum of the reaction solution indicated a conversion of about 25% of the epoxide into p-butyrolactone. After the excess propylene oxide had been taken off, the butyrolactone which remained was admixed with an NMR shift reagent (3) and the NMR spectrum was recorded in a mixture of $CCl_4$/benzene (9:1). The product was enriched in S-β-butyrolactone in an ee of about 8%.

Carbonylation 2

$Na[Co(CO)_4]$ (0.51 mmol) together with rac-propylene oxide (65 ml, 1800 eq.) are placed in a steel autoclave (250 ml) and brought to 10° C. by means of a cryostat. After addition of the Cr-salen complex 2 (322 mg, 0.51 mmol) in a countercurrent of argon, a carbon monoxide pressure of 60–65 bar is set. The mixture is initially stirred at 10° C. for 10 minutes, after which the carbonylation is carried out at 50° C. over a period of 4 hours. The reaction was stopped by cooling to 0° C. and reducing the pressure to ambient pressure, and the resulting reaction solution was analyzed. An NMR spectrum of the reaction solution indicated a conversion of about 7% of the epoxide into β-butyrolactone. After the excess propylene oxide had been taken off, the butyrolactone which remained was admixed with an NMR shift reagent (3) and the NMR spectrum was recorded in a mixture of $CCl_4$/benzene (9:1). The product was enriched in S-β-butyrolactone in an ee of about 14%.

Comparative Example using a Salen-Aluminum Complex Without Chiral Induction

The Al-salen complex (4): (1R,2R)-(−)-[1,2-cyclohexanediamino-N,N'-bis(3,5-di-t-butylsalicylidene)]aluminum (III) chloride was prepared from the corresponding salen ligand and $(Et)_2AlCl$ in a manner analogous to the literature synthesis of similar compounds [Atwood, D. A.; Jeiger, J. A.; Rutherford, D. *Inorg. Chem.* 1996, 35, 63–70].

Carbonylation 3

The Al-salen complex 4 (234 mg, 0.39 mmol) was added to $Na[Co(CO)_4]$ (0.39 mmol) in rac-propylene oxide (16 ml, 640 eq.) while cooling in ice and under an argon atmosphere. To charge the steel autoclave (100 ml), it was firstly evacuated and the starting materials were introduced under a countercurrent of argon. After the solution had been introduced, a carbon monoxide pressure of 60–65 bar was set, and the carbonylation was carried out at 50° C. over a period of 3 hours. The reaction was stopped by cooling in ice and reducing the pressure to ambient pressure, and the resulting reaction solution was analyzed. An NMR spectrum of the reaction solution indicated a conversion of about 11% of the epoxide into β-butyrolactone. After the excess propylene oxide had been taken off, the butyrolactone which remained was admixed with an NMR shift reagent (3) and the NMR spectrum was recorded in a mixture of $CCl_4$/benzene (9:1). There is no enrichment in one enantiomer of β-butyrolactone.

Isolation of BL

The reaction mixture from carbonylation 2 is introduced into a distillation apparatus. PO is distilled off at atmospheric pressure. The volatile part of the residue was firstly distilled in a high vacuum ($10^{-3}$–$10^{-4}$ torr). The recondensed product was subsequently subjected to a fine distillation at 60–63° C. under a pressure of 15 mm of Hg: yield of butyrolactone=2.4 g. $^1$H NMR ($CDCl_3$): δ=1.53 (d, 3H), 3.08 and 3.57 (dd, 1H), 4.7 (m, 1H).

This example shows that butyrolactone can be obtained from the reaction mixture. The method is not restricted in any way and can of course be varied in a customary way.

Polymerization of BL

Butyrolactone (2.0 g) and tetrahexylammonium acetate (10.4 mg) were maintained at room temperature for one week; a sticky substance was formed during this time. The reaction mixture was introduced into methanol, resulting in a sticky phase separating out. This was isolated and dried: yield=369 mg of polyhydroxybutyrate (NMR).

We claim:

1. A process for preparing lactones by catalytic carbonylation of oxiranes using a catalyst system comprising
    a) at least one carbonylation catalyst A comprising uncharged or anionic transition metal complexes of the formula (I)

$$(M_\alpha^{(n+)})_m[M_\beta(L)_4]_l \quad (I)$$

where
    $M_\beta$ Re, Co, Ru, Rh, Fe, Ni, Mn, Mo, W or mixtures thereof with the formal charge −1,
    L is $PR_3$, $P(OR)_3$, $NR_3$, $SR_2$, $OR_2$, CO, R—CN, R—$NO_2$, (RO)(R'O)C=O, (R)(R')C=O, (R)C=O(OR'),
    $M_\alpha$ is a metal of group 1 or 2 of the Periodic Table of the Elements, Zn or Hg, bis(triarylphosphine)iminium, trityl or $T(R)_4$ where
    T is N, P or As,
    R and R' are each, independently of one another, H, alkyl, aryl, alkaryl or aralkyl,
    n and m are each 1 or 2 and
    l is n×m and
    b) at least one chiral Lewis acid B of the formula $LnMX_m$ where
    M=Mg, Ca, Sc, Y, rare earth element, Ti, V, Cr, Mn, Fe, Co, Ni, Cu, Zn, Al, Ga, Zr, Nb, Mo, Ru, Rh, Pd, Ag, Cd, In, Hf, Ta, W, Re, Os, Ir, Pt, Au, Hg, Tl, Pb, which are present in coordinatively unsaturated form under the reaction conditions,
    X=halide, sulfate, sulfite, nitrate, nitrite, carboxylate, sulfide, phosphate, sulfonate, borate,
    L(n)=phosphine, cyclopentadienyl or ansa-ligands, salen, imines, oxazoline, alkoxide, phenoxide, carboxylate, where various L can also be joined to to one another and L is chiral,
    with the exception of [(salph)Al(THF)$_2$][Co(CO)$_4$], as catalyst, wherein the lactones are mixtures of S- and R-lactones having an excess of one enantionmer.

2. A process as claimed in claim 1, wherein the ligands in the carbonylation catalyst A are uncharged ligands.

3. A process as claimed in claim 1, wherein Co is present as transition metal in the carbonylation catalyst A.

4. A process for preparing catalysts as defined in claim 1 by mixing the components A and B.

5. A process as claimed in claim 1, wherein $M_\alpha$ is lithium, sodium, potassium or cesium.

6. A process as claimed in claim 1, wherein said anionic transitional metal complex is tetraphenylphosphonium tetracarbonylcobaltate, tetraphenylarsenium tetracarbonylcobaltate, tetraphenylammonium tetracarbonylcobaltate, tetraethylphosphonium tetracarbonylcobaltate, tetraethylarsenium tetracarbonylcobaltate and tetraethylammonium tetracarbonylcobaltate or sodium tetracarbonylcobaltate.

* * * * *